US006218104B1

(12) United States Patent
Morris et al.

(10) Patent No.: US 6,218,104 B1
(45) Date of Patent: Apr. 17, 2001

(54) METHOD OF DETECTION OF CARCINOGENIC HUMAN PAPILLOMAVIRUS

(75) Inventors: Brian James Morris, Redfern; Brian Nightingale, Burwood, both of (AU)

(73) Assignee: Biosearch International Pty. Ltd., Sydney (AU)

( * ) Notice: Subject to any disclaimer, the term of this patent is extended or adjusted under 35 U.S.C. 154(b) by 0 days.

(21) Appl. No.: 09/000,634

(22) Filed: Dec. 30, 1997

Related U.S. Application Data

(63) Continuation of application No. 07/423,401, filed as application No. PCT/AU88/00047 on Feb. 24, 1988, now Pat. No. 5,783,412.

(30) Foreign Application Priority Data

Feb. 26, 1987 (AU) .................................................... PI0559

(51) Int. Cl.[7] .............................. C12Q 1/70; C12Q 1/68; C12P 19/34
(52) U.S. Cl. .................................... 435/5; 435/6; 435/91.2
(58) Field of Search ................................. 435/6, 91.2, 5

(56) References Cited

U.S. PATENT DOCUMENTS

| 4,683,195 | 7/1987 | Mullis | 435/6 |
| 4,683,202 | 7/1987 | Mullis | 435/91 |
| 5,176,995 | 1/1993 | Sninsky | 435/6 |
| 5,364,758 | 11/1994 | Meijer | 435/5 |

FOREIGN PATENT DOCUMENTS

| 55322 | 3/1986 | (AU) . |
| 55323 | 3/1986 | (AU) . |
| 67109 | 1/1987 | (AU) . |
| 0235004 | 2/1987 | (FR) . |

OTHER PUBLICATIONS

Derwent Abstract of JP 61274697, 1986.
Derwent Abstract of JP 62214355, 1987.
S. T. Cole, et al. "Nucleotide Sequence and Comparative Analysis of the Human Papillomarvirus Type 18 Genome Phylogeny of Papillomaviruses and Repeated Structure of the E6 and E7 Gene Products." J. Mol. Biol. , vol. 193 (1987), pp 599–608.
JO. Danos, et al. "Human Papillomavirus 1a Complete DNA Sequence: a novel type of genome organization among Papovaviridae." The EMBO Journal, vol. 1, No. 2 (1982), pp 231–236.
E. Schwarz, et al. "DNA Sequence and genome organization of genital human papillomavirus type 6b." The EMBO Journal, vol. 2, No. 12 (1983), pp 2341–2348.
S. T. Cole et al. "Genome Organization and Nucleotide Sequence of Human Papillomavirus Type 33, Which is Associated with Cervical Cancer." Journal of Virology, vol. 58, No. 3 (Jun. 1986), pp 991–995.

P. G. Fuchs, et al. "Epidermodysplasia Verruciformis–Associated Human Papillomavirus 8: Genomic Sequence and Comparative Analysis." Journal of Virology, vol. 58, No. 2 (May 1986), pp 626–634.
Griffin N.R. et al., J. Clin. Pathology, 1990, p. 52–56.
Morris B.J. et al, "Automated Polymerase Chain Reaction . . . ", J. Med. Virol. 32: 22–30 (1990).
Saiki, R.K. et al, 1986 "Analysis of Enzymatically Amplified . . . " Nature 324(6093) 163–166.
Young L.S., et al., "The Polymerase Chain Reaction . . . " Brit. Med. J. 298, 14–18, 1989.
Schwarz E., et al, 1983 "DNA Sequence . . . " EMBO J. 21 (12) 2341–2348.
Seedorf et al, 1985, "Human Papillomavirus . . . ", Virol 145: 181–185.
Shibata DK et al 1988 "Dectection of Human Papillomavirus . . . " J. Exp. Med. 167: 225–230.
Boshart, M. et al, "A New Type of Papillomavirus DNA, Its Presence in Genital Cancer Biopsies and in Cell Lines Derived from Cerivical Cancer" The EMBO Journal, vol. 3, No. 5, pp. 1151–1157, 1984.
Chow VTK et al. "*Thermus Aquaticus* DNA Polymerase–Catalysed Chain Reaction for the Detection of Human Papillomaviruses" Journal of Virological Methods, 27 (1990), 101–112.
Chow, V. et al, "Molecular Diagnosis of Genital HPV DNA Types by Polymerase Chain Reaction and Sensitivity–Standardized Filter in . . . " Molecular and Cellular Probes, 1990, 4, 121–131.
Claas, CJE et al, "Human Papillomavirus Detection in Paraffin–Embedded Cervical Carcinomas and Metastases of the Carcinomas . . . " Amerian Journal of Pathology, Vo. 135, No. 4, Oct. 8, 1989, p. 703–709.
Cornelissen, MTE et al, "Localization of Human Papillomavirus Type 16 DNA Using the Polymerase Chain Reaction in the . . . " J. Gen. Viro. 1984, 70, 2555–25.
Dallas, PB et al, "Polymerase Chain Reaction for Fast, Nonradioactive Detection of High and Low–Risk Papillomavirus Types . . . " Journal of Medical Virology, 27: 105–111 (1989).
Dartmann, K. et al, "The Nucleotide Sequence and Genome Organization of Human Papillomavirus Type 11", Virology 151, 124–130, 1986.
Day, PJR, et al "Synthesis in Vitro and Application of . . . " Biochem. J. 1990, 267, 119, 123.
Durst, M et al "A Papillomavirus DNA from a Cervical Carcinoma and its Prevalance in Cancer Biopsy Samples from Different . . . " Proc. Natl. Acad. Sci. USA vol. 80 pp. 3812–3815, Jun. 1983, Medical Sciences.

(List continued on next page.)

*Primary Examiner*—Lisa B. Arthur
(74) *Attorney, Agent, or Firm*—Ladas & Parry

(57) ABSTRACT

High risk carcinogenic human types 16, 18 and 33 are distinguished from low risk human papillomavirus types 6 and 11 in a sample of human cervical tissue. A selected characteristic portion of the E6 region of the virus defined by specific oligonucleotide primers is amplified using a polymerase chain reaction. The presence or absence of the characteristic portion of the E6 region is detected by gel electrophoresis or using a labeled oligonucleotide probe.

4 Claims, 8 Drawing Sheets

OTHER PUBLICATIONS

Gregoire, L et al. "Amplificiation of Human Papillomavirus DNA Sequences by Using Conserved Primers" Journal of Clinical Microbiology, Dec. 1989, p. 2660–2665.

Harju, L et al., "Affinity–based collection of amplified viral DNA: application to the detection of human . . ." Molecular and Cellular Probes, 1990, 4, 223–235.

Matlashewski, G. et al, "The Expression of Human Papillomavirus Types 18 E6 Protein in Bacteria and the Production of Anti–E6 Antibodies" J. Gen. Viro 1986, 67, 1909–1916.

McNicol, PJ et al. "Detection of Human Papillomavirus DNA in Prostate Gland Tissue by Using the Polymerase Chain . . ." Journal of Clinical Microbiology, Mar. 1990, p. 409–412.

Meanwell, CA "The Epidemiology of Human Papillomavirus Infection in Relation to Cervical Cancer", Cancer Surveys, vol. 7. No. 3, 1988, pp. 486–487.

Melchers, W J G et al, "Human Papillomavirus Detection in Urine Samples from Male Patients by the Polymerase Chain . . ." Journal of Clinical Microbiology, Aug. 1989, p. 1711–1714.

Roman, A et al "Human Papillomaviruses: Are We Ready to Type?", Clinical Microbiology Reviews, Apr. 1989, p. 166, 176, 177.

Saiki, RK et al, "Enzymatic Amplification of β–Globin Genomic Sequences and Restriction Site Analysis for Diagnosis of Sickle Cell Anemia", Science, vol. 230, 1985, pp. 1350–1354.

Scharf, S.J. et al, "Direct Cloning and Sequence Analysis of Enzymatically Amplified Genomic Sequences", Science, vol. 233 1986, pp. 1076–1078.

Snijders, P.J.F. et al., "The Use of General Primers in the Polymerase Chain Reaction Permits the Detectection of Broad . . ." Journal of General Virology, 1990, 71, p. 173–181.

Ting, Y. et al. "Detection and Typing of Genital PCR Protocols: A Guide to Methods and Applications", 1990, pp. 356–367.

Van Den Brule, A.J.C. et al., "General Primer–Mediated Polyermase Chain Reaction Permits the Detection of Sequenced . . ." Int. J. Cancer, 45, 1990, pp. 644–649.

Merz, B. "DNA Probes for Papillomavirus Strains Readied for Cervical Cancer Screening" Medical News & Perspectives, JAMA, vol. 260, No. 19, 1988, p. 2777.

"Human Papillomavirus DNA Detection Kit" Vira, Pap. Pp. Title–20.

Beyer–Finkler, E. et al., "Anti–contamination Primers to Improve Specificity of Polymerase Chain Reaction in Human . . ." Lancet, vol. 335/8700, 1990, pp. 1289–1290.

Xiao, X. et al., "Papillomavirus DNA in Cervical Carcinoma Specimens from Central China", the Lancet, 1988, p. 902.

Enzo Diagnostics, Inc. "DNA Probe–Based Assay".

Perkin Elmer Pty. Ltd., Gene Amplimer HPV Primer 1(MY09) 1990, 2 pages.

Morris, BJ et al., "Papillomavirus Screening of Cervical Lavages by Polymerase Chain Reaction", the Lancet, 1988, p. 1368.

Manos, M. et al., "Looking for Human Papillomavirus Type 16 by PCR", the Lancet, 1990, p. 734.

Ward, P. et al., "Human Papillomavirus Subtype 16a", the Lancet, 1989, p. 170.

Yoshikawa, H. et al., "Amplification and Typing of Multiple Cervical Cancer Associated Human Papillomavirus DNA's Using . . ." International Journal of Cancer, 1990, p. 990–992.

Tidy, J. et al, "High Rate of Human Papillomavirus Type 16 Infection in Cytologically Normal Cervices", The Lancet, 1989, p. 434.

Tidy, J. et al, "Retraction: Human Papillomavirus Subtype 16b", The Lancet, 1989, p. 1535.

Tidy, J. et al, "A New and Sensitive Method of Screening for Human Papillomavirus Infection", Obstetrics & Gynecology, 1989 pp, 410–414.

Tidy, J. et al, "Relation Between Infection with a Subtype of HPV16 and Cervical Neoplasia", The Lancet, 1989, pp. 1225–1227.

Queen, C. Nucleic Acids Research, (1984), vol. 12(1), p. 581–599.

AMPLIFICATION PRODUCT

PRIMERS 120 bp HPV6/11 AMP. PRODUCT

PRIMERS

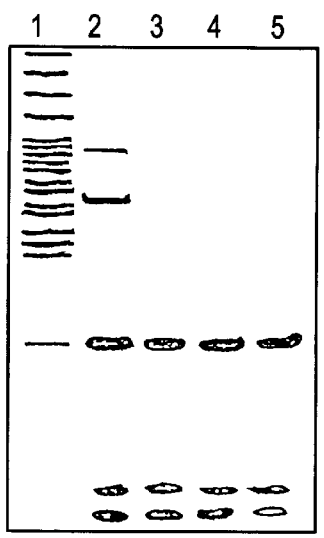
HPV16/33 AMPLIFICATION PRODUCT (FAINT); 200 bp
HPV6/11 AMPLIFICATION PRODUCT (DARKER); 120 bp
PRIMERS
FIG. 16
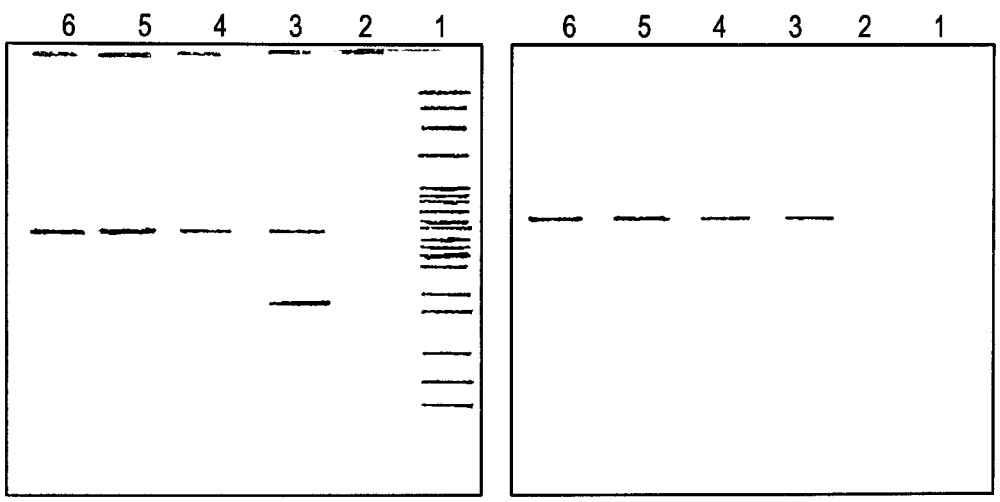
FIG. 17
FIG. 18
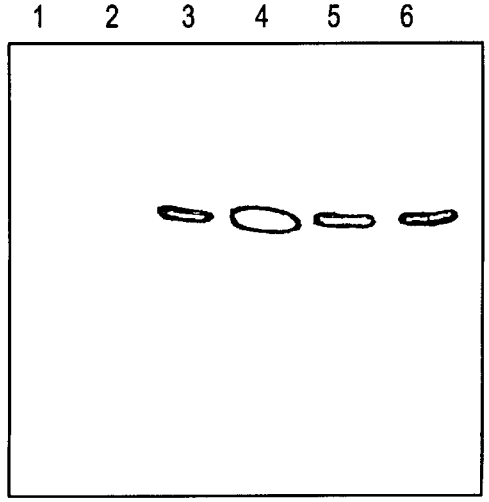
FIG. 19

METHOD OF DETECTION OF CARCINOGENIC HUMAN PAPILLOMAVIRUS

This is a continuation of application Ser. No. 07/423,401 filed on Aug. 25, 1989, now U.S. Pat. No. 5,783,412, which is a 371 of PCT/AU88/00047 filed Feb. 24, 1988, claims the benefit thereof and incorporates the same by reference.

TECHNICAL FIELD OF INVENTION

This invention relates to a method for the specific detection of the DNA of papillomaviruses in clinical samples. In particular, the test aims to differentiate, in the shortest possible time, whether cells from the anogenital region contain types of papillomavirus that are associated with benign lesions. Such differentiation has important implications in patient evaluation and follow-up.

BACKGROUND

Cancer of the cervix is the most common cancer in women (~25% of all female cancer). Moreover, the incidence is increasing in younger women. Indeed, approximately 2% of routine cervical smears show abnormal cytology, indicating an epidemic. Such an epidemic is current in many western and developing countries. Sexual activity appears to be an important predisposing factor in the epidemiology of cardinogenesis and precancerous lesions. An early age of sexual intercourse and multiplicity of sexual partners are associated statistically with an increased risk of malignancy [Harris et al., Br. J. Cancer 42: 359–63, 1980]. The consorts are often men with penile warts ("high risk males"), and a very high proportion (>90%) of cervical carcinoma tissue contain detectable DNA sequences for known varieties of the human papillomavirus (HPV). This supports a growing body of evidence implicating certain types of HPV as the sexually transmitted factor involved in the development of squamous-cell carcinoma of the cervix [zur Hausen et al., Progr. Med. Virol. 30: 170–86, 1984; zur Hausen, Prog. Med. Virol. 32: 15–21, 1985; zur Hausen, Cancer 59: 1692–6; Campion et al., Lancet 1: 943–6, 1985]. The prevalence of cervical cancer and precancerous lesions is becoming increasingly more common in younger women. Without treatment it can be fatal, the death rate being ~100 per million women per year in Western countries. Fortunately, if detected at an early stage, effective treatment is available that can eliminate the fatal consequences.

The immediate management and subsequent follow-up of young women with abnormal cytological smears who still wish to bear children presents many problems. This has been compounded by uncertainty about the interpretation of smears with features of papillomavirus infection ("kollocytes") as well as dysplasia. Moreover, the current cytological testing tool for cervical cancer screening, the Pap smear, has a false negative rate of ~20%. Significant numbers of dysplastic lesions regress spontaneously, others fail to progress, while a few progress rapidly. Thus, from an ill-defined cloud of morphological abnormalities occasional cancers develop. At present there is no clear way to predict whether cancer will result if a Pap smear happens to be abnormal. Clinical examination of many of these patients has failed to find warty lesions (condylomata accuminata) on the external genitalia or, indeed, on the cervix itself. The more difficult procedure of colposcopy, after the application of 3% acetic acid, is, in fact, required, revealing the presence of flat ("non-condylomatous") warts (which are invisible to the naked eye). These are the expected premalignant lesions. Histophathological progression of the wart to carcinoma in situ and frank malignancy has been well described [e.g., Dyson et al., J. Clin. Path. 37: 126–31, 1984]. An increasingly prevalent problem is the occurrence of invasive cancer within 3 years of a negative Pap smear [Berkowitz et al., Gynecol. Oncol. 8: 311, 1979; Holman et al., Med. J. Aust. 2: 597, 1981]. Whereas the presence of papillomavirus replication may be confirmed in cervical condylomata by detection of virus particles or the group-specific antigen, neither particles nor antigen have, however, been found in squamous cell carcinoma tissue.

In contrast to the uncertainty and controversy that surrounds the interpretation of tests based on morphology, the new techniques in molecular biology can be utilised to bypass such problems and provide more objective information. By using nucleic acid hybridization techniques the viral DNA can be identified directly and at an earlier stage of infection. Indeed, using these approaches, HPV types have been found in both benign and premalignant lesions.

At present ~50 types of the papillomavirus have been distinguished in human infection. Different ones infect different epithelial areas. The particular types of HPV that commonly infect the genital tract include those assigned the numbers 6, 11, 16, 18 and several rarer types (31, 33, 35, 39, 43 and 44). HPV6 [de Villlers et al., J. Virol. 40: 932–5, 1981] and HPV11 [Gissmann et al., J. Virol. 44: 393–400, 1982; Gissman et al., Proc. Natl. Acad. Sci. USA 80: 560–3, 1983; Dartmann et al., Virology 151: 124–30, 1986] have been associated with benign condylomata accuminata, the classical lesion of the anal and genital tract [Gissmann et al., J. Invest. Dermatol. 83: 26s–8s, 1984]. In contrast, HPV16 [Durst et al., Proc. Natl. Acad. Sci. USA 80: 3812–5, 1983] and HPV18 [Boshart et al., EMBO J. 3: 1151–7, 1984; Cole and Danos, J. Mol. Biol. 193: 599–608, 1987] are more often detected in dysplastic flat lesions of the vulva and cervix, and squamous carcinoma of the cervix and penis [Crum et al., Cancer 49: 468–71, 1982; Campion et al., Lancet i: 943–6, 1985].

Thus the types of HPV that infect the anogenital area can be assigned to two categories as follows:
1. "Low-risk"; HPV 6 and HPV11, with type 6 being the most common of all anogenital types.
2. "High-risk"; HPV16, HPV18, HPV31, HPV33, HPV35, HPV39 HPV43 and HPV44.

The frequency of occurence of the higher risk types is in decreasing order. Thus, within the high risk category, HPV16 is most common (45–60%), HPV18 is next most common (20–30%) and the others are rarer, the last 4 being discovered only recently and reported in 1986 (total frequency for all of these rarer types is, collectively, ~15%). Other rarer types are likely to be discovered in due course.

In support of a role for HPVs in cervical cancer the following findings are noteworthy:

(i) DNAs of known high risk HPVs have been detected in ~90% of cervical adenocarcinomas and squamous cell carcinomas [Zachow et al., Nature 300: 771–3, 1982; Gissmann et al., 1984, ibid].

(ii) High risk HPV DNA has been found in metastases arising from cervical tumours [Lancaster et al., Am. J. Obstet. Gynecol. 154: 115–9, 1986].

(iii) Instead of being present in cells in the usual episomal form, DNAs of high risk HPVs have been found integrated into human genomic DNA [Schwartz et al., Nature 314: 111–4, 1985; Lehn et al., Proc. Natl. Acad. Sci. USA 82: 5540–4, 1985; Kreider et al., Nature 317: 639–41, 1985; Matsukura et al., J. Virol. 58: 979–82, 1986; Schneider-Gadicke and Schwartz, EMBO J. 5: 2285–92, 1986; Di Luca et al., *J. Gen. Virol.* 67: 583–9, 1986]. Such integration has been suggested to be necessary for malignant conversion of the cells, supported by findings of integration also in pre-carcinoma tissue [Shirasawa et al., *J. Gen. Virol.* 67: 2011–5, 1986].

(iv) The integration pattern usually interrupts or deletes specific regions of the HPV16 or 18 DNA, but consistently leaves intact the E6 and E7 openreading frames (ORFs) ([Pater and Pater, *Virology* 145: 313–8, 1985], which continue to express, at least in cell lines derived from cervical carcinomas [Smotkin and Wettstein, *Proc. Natl Acad. Sci. USA* 83: 4680–4, 1986; Androphy et al., *EMBO J.* 6: 989–92, 1987; Baker et al., *J. Virol.* 61: 962–71, 1987; Takebe et al., *Biochem. Biophys. Res. Commun.* 143: 837–44, 1987].

(v) A splice donor exists in the E6 ORF of HPV16 and 18 (but not HPV6 and 11) which can result in the generation of an ORF which when translated resembles epidermal growth factor [zur Hausen, *Lancet* 489–91, 1986].

(vi) Integration in cervical cell lines (HeLa, CaSki, SiHa, SW756, etc) is often near proto-oncogenes [Dürst et al., *Proc. Natl. Acad. Sci. USA* 84: 1070–4, 1987; Popescu et al., *Cytogenet. Cell Genet,* 44: 58–62, 1987; Popescu et al., *J. Virol,* 51: 1682–5, 1987; Shirasawa et al., *J. Gen. Virol.* 68: 583–91, 1987].

(vii) Such integration is associated with increased expression of c-myc and c-ras mRNA [Dürst et al., 1987, ibid; Shirasawa et al., 1987, ibid.), consistent with the suggestion that cis-activation of cellular oncogenes by HPV might be associated with malignant transformation of cervical cells.

(viii) Human fibroblasts and keritanocytes can be transformed by transfection with HPV16 [Pirisi et al., *J. Virol.* 61: 1061–6, 1987], as can NIH 3T3 cells [Tsunokawa et al., *Proc. Natl. Acad. Sci. USA* 83: 2200–3, 1986; Yasumoto et al., *J. Virol.* 57: 572–7, 1986].

(ix) Integration might disrupt genes coding for cellular interfering factors: this may cripple the cells normal defense mechanism that suppresses uncontrolled growth and transcription of the virus [zur Hausen, *Lancet* 489–91, 1986].

Whereas penile warts in males only very rarely result in cancer of the penis, when transmitted to the cervix cancer is much more likely to follow. About one-third of patients who have histologically-confirmed HPV infection of the cervix can be expected to develop cervical intraepithelial neoplasia (CIN) within a year [Nash et al., *Obstet. Gynecol.* 69: 160–2, 1987]. The lag time between infection and cancer is, however, often 10–30 years. Thus the unique environment of the cervix, coupled with other factors, such as smoking [Trevathan et al., *J. Am. Med. Ass.* 250: 449–504, 1983], also contributed to the onset of the cancer. Damage of DNA by the latter, coupled with HPV's action to cause cellular proliferation, may explain the onset of malignancy. Treatment of women with precancerous lesions involves surgical extirpation of the affected area. Moreover, it is now believed by many that treatment should also involve her infected male consort, in order to avoid reinfection and infection of other women by the man.

Since the cytological test used presently for routine screening of cervical cells (Pap smear) is considered subjective and does not allow the identification of the particular type of HPV in a lesion, we foresee that the more specific approach of DNA—DNA hybridization for direct viral detection will in due course be used routinely to supplement or even replace cytology in primary screening.

In the clinical evaluation of a patient it is important to distinguish between those lesions harbouring the potentially carcinogenic (high-risk) types from those associated with the more benign (low-risk) types.

The evaluation of patient specimens for HPV infection has been facilitated by techniques of filter hybridization. Such techniques have been used to detect HPV DNA in cervical scrapes collected in parallel with samples for routine cytology [Wagner et al., *Obstet. Gynecol.* 64: 767–72, 1984; Wickenden et al., *Lancet* i: 65–7, 1984; Schneider et al., *Science* 216: 1065–70, 1982]. In January 1985 a project was begun by Dr. Morris at the University of Sydney to develop a direct test for the anogenital types of HPV; with a particular aim of evaluating whether the infection was by one of the high risk types of HPV or by one of the low risk types. The first publication describing a preliminary version of the test, which involved recombinant viral DNAs, is: B. R. Henderson, C. H. Thompson, B. R. Rose, Y. E. Cossart and B. J. Morris, "Detection of specific types of human papillomavirus in cervical scrapes, anal scrapes, and anogenital biopsies by DNA hybridization", *Journal of Medical Virology* 12: 381–93, 1987. This paper was submitted early in 1986. Since then the sensitivity of the recombinant DNA test has been increased 100-fold and further improvements are being made continually. Over 5,000 clinical specimens have been tested to date. These have been mainly from Sydney S.T.D. clinics. The data so far has established the viability and usefulness of direct viral detection for determination of the presence and nature of HPV infection in cervical scrapes and other anogenital specimens. Our other recent publications using this approach include: B. R. Rose, C. H. Thompson, A. M. McDonald, B. R. Henderson, Y. E. Cossart & B. J. Morris, "Cell Biology of cultures of anogenital warts", *British Journal of Dermatology* 116: 331–22, 1987; B. J. Parker, Y. E. Cossart, C. H. Thompson, B. R. Rose & B. R. Henderson, "The clinical management and laboratory assessment of anal warts", *Medical Journal of Australia* 147: 59–63, 1987; P. M. Katelaris, Y. E. Cossart, B. R. Rose, B. Nightingale, E. Sorich, C. H. Thompson, P. B. Dallas & B. J. Morris, "Human papillomavirus: The untreated male reservoir", *Journal of Urology, in press,* 1988. Much other work has yet to be published.

For main strand DNA sequences of the most common anogenital HPV types see as follows:

The sequence of HPV6b is given in Schwartz et al., *EMBO J.* 2: 2341–2348.

The sequence of HPV11 is given in Dartmann et al., *Virology* 151: 124–30, 1986.

The sequence of HPV16 is given in Seedort et al., *Virology* 145: 181–5, 1985.

The sequence of HPV18 is given in Matlashewski et al., *J. Gen. Virol.* 67: 1909–16, 1986.

The sequence of HPV33 is given in Cole and Streeck, *J. Virol.* 58: 991–5, 1986.

Principal of detection of specific viral DNA by hybridization

DNA is double-stranded. Each strand of DNA is a complementary 'mirror image' of the other. The DNA strands are held together by hydrogen bonding. Our techniques for detecting viral DNAs are based on the ability of the unique sequence of nucleotides in a DNA strand to bond with ('hybridize') to a sequence complementary to it. Thus, armed with a DNA sequence for all or a unique part of a papillomavirus type, it is possible to use this as a 'homing probe' in order to detect the virus in a sample of cervical cells from a patient. The DNA for use as probe is labelled either with a radioactive isotope or nonradioactive label so that it can be detected later. To increase the sensitivity of the test we have utilized a method for amplification of the HPV DNA sequences in the sample.

Background to approach used to amplify viral DNA

In order to increase the sensitivity of the detection technique we use a method described originally for diagnosis of genetic diseases. This is known as a 'polymerase chain reaction' (PCR). It is used to amplify enzymatically a specific DNA sequence before hybridization with synthetic oligonucleotide probe. A typical amplification factor is ~250,000 copies starting from one copy of viral DNA. Such an approach not only increases sensitivity, but fulfills requirements of specificity, speed, simplicity, and amenability to nonradioactive detection methods expected of a more versatile testing procedure. It is also amenable to assembly as a kit and to automation, both of which we have accomplished. The PCR technique is described in papers that deal with prenatal diagnostic testing for specific genetic abnormalities [Sakii et al., *Science* 230: 1350–4, 1985; Sakii et al., *Nature* 324: 163–6, 1986; Scharf et al., *Science* 233: 1076–8, 1986]. The PCR technique is the subject of the following: Australian Patent Application AU-A-55322/86, Cetus Corp." Process for Amplifying Nucleic Acid Sequences", U.S. Priority Date 28.3.85; Australian Patent Application AU-A-55323/86, "Amplification and Detection of Target Nucleic Acid by Hybridization Probe", U.S. Priority Date 28.3.85.

Briefly, a small, unique portion of the HPV DNA sequence, ~100–200 bp long, is amplified by the PCR procedure. In the examples a region in the E6 region has been chosen. However, any other region in the viral DNA may also be chosen. The PCR step requires two ~20 mer oligonucleotide primers that flank the region to be amplified. One primer is complementary to the (+)-strand of a region of the DNA and the other is complementary to the (−)-strand. The annealing of primer to the (+)-strand of denatured sample viral DNA, followed by extension with, e.g., the Klenow fragment of *Escherichia coli* DNA polymerase, or other enzymes that carry out a similar reaction, and deoxynucleotide triphosphates results in the synthesis of a (−)-strand fragment containing a 'target' sequence residing between the hybridization sites of the primer. At the same time a similar reaction occurs with the other primer, creating a new (+)-strand. The principle of the method is shown in the following diagram.

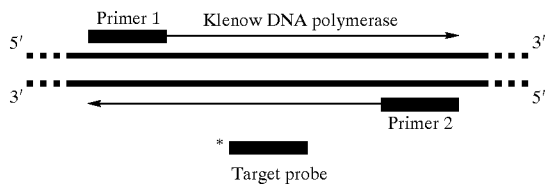

Since these newly-synthesized DNA strands are themselves templates for the PCR primers, repeated cycles of denaturation, primer annealing, and extension result in the exponential accumulation of the ~100–200 bp region defined by the primers. Next, the specific DNA is detected. Various means are possible for doing this. The amount of DNA produced may be sufficient for direct visualization after electrophoresis on a gel and staining.

BRIEF DESCRIPTION OF THE DRAWINGS

FIG. 7 also indicates that the HPV16/33 oligonucleotide probe not hybridize to other HPV types (Lanes 5,6,7).

FIG. 16 indicates that the PCR primers for different HPV types can be used in the same reaction mixture to generate amplification products unique for each HPV type. HPV6/11 and HPV16/33 primers were used in the same reaction mixture. Lane 2 shows HPV16/33 amplification product and HPV6/11 amplification product.

FIG. 17 indicates the PCR amplification of HPV16/33 DNA from various sources.

FIG. 18 indicates the hybridisation of alkaline phosphatase probes with the HPV16/33 DNA from FIG. 17.

FIG. 19 indicates the hybridisation of radioactively labelled probes with HPV16/33 DNA from FIG. 17.

DISCLOSURE OF THE INVENTION

Figure 1:
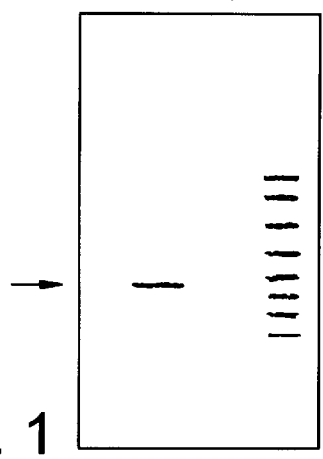
FIG. 1 indicates the amplification of pure HPV16 DNA using PCR relative to a standard restriction of pBR322 with HpAII.

In particular, the present invention provides a method of detection of carcinogenic human papillomavirus HPV16 and/or HPV18 which comprises
  (a) applying a polymerase chain reaction technique to a sample of human cervical tissue cells so as to amplify the amount of a selected characteristic DNA portion of any such carcinogenic HPV present comprising the steps of:
    (i) heating to dissociate the DNA strands,
    (ii) adding oligonucleotide primers defining each end of said characteristic DNA portion,
    (iii) cooling to allow the primers to anneal to the dissociated DNA strands,
    (iv) adding a DNA polymerase,
    (v) at the cooled temperature allowing formation of DNA complementary to each strand of said characteristic DNA portion,
    (vi) heating to dissociation temperature, and repeating steps (iii) to (vi), optionally omitting step (iv) where a heat stable DNA polymerase is used.
  (b) detecting the present/absence in the amplified sample of said characteristic DNA portion characteristic of HPV16 or HPV18.

The invention also extends to the specific oligonucleotide primers used, and to specific labelled oligonucleotide probes, as described hereinafter.

Embodiments of this invention will now be described by way of example only.

EXAMPLES

Summary of typical technique(s) used

1. Scrapes or wart tissue are collected in the clinic by routine methods and stored, if necessary, for up to 3 days before transport to the laboratory for analysis.
2. Cells are lysed and their DNA denatured.
3. Viral DNA is amplified by a polymerase chain reaction.
4. Viral DNA is detected directly, e.g., by electrophoresis and staining [=end-point of test],
OR
4a. Samples (multiple) are applied to a charged nylon membrane using a dot manifold, along with appropriate standards and controls.
5. Filter is prehybridized.
6. Filter is hybridized with labelled mixed viral DNA probes, one mixture containing probes for the 'high risk' (potentially carcinogenic) and the other probes for the 'low risk' HPVs.
7. Filters are washed under conditions of appropriate stringency where only closely related sequences will remain attached (through hydrogen bonding of the complementary DNA strands of each).
8. Autoradiography, (Black spots of exposure on the X-ray film where a sample has been applied shows that it contains a HPV virus of the category probed for.), OR 8a. Perform nonradioactive detection method. (Coloured spot or other signal, as appropriate, shows that it contains a HPV virus of the category probed for.)
Examples of oligonucleotides that work in test described
PRIMERS For each HPV type or category two synthetic oligonucleotides are synthesized for sue as primers in the extension and amplification step of PCR. These oligonucleotides correspond to DNA flanking a specific "target" sequence of interest, this being a sequence of DNA in the viral genome that is unique for HPV and differs from one HPV type or category ('high risk' vs 'low risk') to the next. We have found the oligonucleotides described below to be suitable; however, other appropriate sequences can also be chosen for the specific viral types indicated or for other types of papillomavirus.
Low risk HPVs For HPV6 and HPV11 a suitable target sequence has been chosen within the E6 open reading frame of the viral genome. Suitable DNA sequences flanking this target sequence for use as primers are as follows (where position number refers to the nucleotide sequence of the viral genome) and are the same for each of these HPVs:
  HPV1/11 primer 1: $^{5'}$ATGCCTCCACGTCTGCAAC$^{3'}$ POSITION: 115 133
  HPV6/11 primer 2: $^{3'}$TACGTGACTGGTGGGCGTCTC$^{5'}$POSITION: 208 227

These primers have complementary sequences on HPV6 and HPV11. They differ from sequences in the genomes of HPV16, HPV18 and HPV33, where separate primers flanking a chosen DNA target sequence are synthesized for these, together with oligonucleotides suitable for use as probes, using the same principal as described above and below, respectively, for HPV6 and HPV11.
High risk HPVs For HPV16 and HPV33 suitable sequences flanking a chosen target sequence are as follows:
  HPV16/33 primer 1: $^{5'}$TGAGGTATAT-GACTTTGCTTTT$^{3'}$ POSITION: 223 244
  HPV16/33 primer 2: $^{3'}$AATTAATCCACATAAT$^{5'}$ POSITION: 401 416

For HPV18 suitable sequences flanking a chosen target sequence are as follows:
  HPV18 primer 1: $^{5'}$ACAGTATTGGAACTTACAGA$^{3'}$ POSITION: 418 437
  HPV18 primer 2: $^{3'}$TTTACATATCTAAAAATAAG$^{5'}$ POSITION: 508 527

It is most convenient to add primers for all HPV types to each sample. The sample may then be divided and probed for each category of HPV types (high risk vs low risk).
TARGET OLIGONUCLEOTIDES FOR USE AS PROBES
Low risk HPVs Synthesize oligonucleotide (target) sequence for use as probe. This corresponds to a region between the two primers, and is identical for each of the viral types HPV6 and HPV11, but differs, of course, from any other viral or other DNA sequence. These sequences are as follows:
  HPV6/11 target oligonucleotide: $^{5'}$GCAAGACGTT-TAATCT$^{3'}$ POSITION: 151 166

For detection of HPV16 and HPV33 the following oligonucleotide (target) sequence is synthesized for use as a probe:
  HPV16/33 target oligonucleotide: $^{5'}$GTGAGTATAGA-CATTAT$^{3'}$ POSITION: 324 340

For detection of HPV18 specifically, or within the category of high-risk HPVs, the following oligonucleotide (target) sequence is synthesized for use as a probe:

HPV18 target oligonucleotide: 5'GATTTATTTGTGGTG-
TATAGA3' POSITION: 460 480

The exact location of all of these sequences may be seen by examination of the published sequences of the viral genomes. It should be emphasized that this same principle, namely synthesis of oligonucleotides that will hybridize to opposite strands of the DNA flanking a specific target sequence in HPV described in the publications listed above and in sequences of other HPVs when published.

Labelling target oligonucleotides

Radioactive labelling

5= end label the ~30 mers with [γ-$^{32}$P]dATP using T4 polynucleotide kinase [Berkner and Folk, *J. Biol. Chem.* 252: 3176–80, 1977]. A kit is available from Dupont (new England Nuclear) that can be used for this step.

i. Mix:

| | |
|---|---|
| DNA with 5' terminal phosphates | 1–50 pmoles |
| 10 x exchange reaction buffer* | 5 μl |
| 5 mM ADP | 3 μl |
| [γ-$^{32}$P]dATP (sp. act. 3000 Cl/mmol) | 100 pmoles (i.e., 30 μl of a 10 mCi/ml solution) |
| Distilled water | to 50 μl |
| T4 polynucleotide kinase | 1 μl (20 units) |
| *10x Exchange reaction buffer: | 0.5 M imidazole.Cl (pH 6.6) |
| | 0.1 M MgCl$_2$ |
| | 50 mM dithlothreitol |
| | 1 mM spermidine |
| | 1 mM EDTA | ii. Incubate at 37° C. For 30 minutes.
iii Add 2 μl of 0.5 M EDTA.
iv. Extract once with phenol/chloroform.

Nonradioactive labelling

Various methods are becoming available for nonradioactive labelling of oligonucleotides for use as hybridization probes. These are more appropriate for use in a HPV detection kit as they generally have acceptably long half-lives and avoid dangers from and the need for a license for use of radioactivity. We have used non-radioactive oligonucleotides made by one such new technique (performed by BRESA, Adelaide) in which alkaline phosphatase is coupled directly to the target oligonucleotide. Alkaline phosphatase labelled oligonucleotides of any sequence specified are available made-to-order from BRESA.

Reagents

Collection buffer=phosphate buffered saline (PBS)=140 mM NaCl, 3 mM KCl, 8 mM Na$_2$HPO$_4$, 12H$_2$O, 1.5 mM KH$_2$PO$_4$.
Lysis buffer=50 mM NaCl, 50 mM Tris, pH 7.5, 0.5% SDS, 10 mM EDTA.
Enzyme powder=Proteinase K (concentration after addition of 10 ml lysis buffer=50 μg/ml)
Deproteinization reagent 1=phenol/chloroform/isoamyl alcohol (25:24:1, v/v)
Deproteinization reagent 2=chloroform/isoamyl alcohol (24:1, v/v)
Extraction solution=3 M sodium acetate
PCR buffer (if using normal Klenow)=50 mM NaCl, 10 mM Tris.HCl, pH7.6, 10 mM MgCl$_2$.
PCR buffer (if using heat stable DNA polymerase)=50 mM Tris.HCl, pH 8.8 (at 25° C.), 10 mM ammonium sulphate, 10 mM MgCl$_2$.

| PCR reagent buffer = | |
|---|---|
| 10 x PCR buffer | .10 μl |
| dNTPs | 16 μl (4 μl of each 50 mM stock) |
| Dimethylsulphoxide | 10 μl |
| Primers | 1 μl of each 500 ng/μl stock (= 4 μl in total) |
| DNA (cells or DNA) | x μl |
| dH$_2$O | Make volume up to 100 μl |

DNA polymerase solution=1 U/μl of DNA polymerase (Klenow fragment)
Prehybridization solution=6×SSC, 25×Denhardt's solution, 0.5% sodium dodecyl sulphate.

| | |
|---|---|
| Hybridization solution = | 6 x SSC, 1 x Denhardt's solution and 0.5% SDS, with 100 ng/ml alkaline phosphatase linked oligonucleotide probe. |

Wash solution 1=6 x SSC, 0.1% SDS
Wash solution 2=6 x SSC
Wash solution 3=1 M NaCl, 0.1 M Tris.HCl, pH 9.5, 5 mM MgCl$_2$
Colour reagent solution=0.33 mg/ml nitroblue tetrazollium (NBT), 0.17 mg/ml 5-bromo-4-chloro-3-indoyl phosphate (BCIP), 0.33% v/v dimethylformamide in 0.1 M Tris.HCl, pH 9.5, 0.1 M NaCl, 5 mM Mg Cl$_2$
TE=10 mM Tris.HCl, pH 8.0, 1 mM EDTA
SSC=standard saline citrate (1 x SSC=0.15 M sodium chloride, 0.015 M trisodium citrate, pH 7.0)

| | |
|---|---|
| Denhardt's solution = | 5 g Ficoll, 5 g polyvinylpyrrolldone, 5 g bovine serum albumin, made up to 500 ml with distilled water. |

SDS=sodium dodecyl sulphate
PROTOCOL FOR CERVICAL or other anogenital, SCRAPES
Collection of specimen from patient
 1. Collect scrape from the patient in the clinic using a speculum (i.e., as for a Pap smear) or, preferably, by cervicovaginal lavage in the case of cervical screening.
 2. Place the stick with scrape in collection tube provided. (This tube contains sterile collection buffer.)
 3. The scrape tissue may be kept at 4° C. for 2–3 days or frozen at −20° C. for longer term storage.
Sample preparation
 1. Take collection tube and shake off residual cells on speculum into collection buffer in tube. Pour suspension into an Eppendorf tube.
 2. Microfuge for 15 seconds. Pour off PBS from pellet. Resuspend cells in 500 μl fresh collection buffer by vortexing briefly, Microfuge again.
 3. Repeat step 2 two more times.
 4. Determine number of cells per ml using a haemocytometer.
Procedure for polymerase chain reaction (Normal Klenow)
 1. Add a volume of cell suspension that contains ~10,000 cells to 35 μl distilled water in an Eppendorf tube.
 2. Place tube in water bath heated to 95–98° C.
 3. After 10 minutes remove tube and microfuge briefly to remove condensation.
 4. Immediately add 65 μl PCR reagent buffer.
 5. Place tube in a second water bath heated to 37° C.

6. After 2 min add 1 µl DNA polymerase solution; allow reaction to procede for 2 min at 37° C.

7. Place tube back in 95–98° C. water bath for 2 minutes, then microfuge briefly.

8. Repeat steps 5–7 twenty five times.

Procedure for polymerase chain reaction (Thermophilic polymerase from *Thermus aquaticus*)

A DNA polymerase that is resistant to 95° C. is used instead. Use of this enzyme facilitates the test to some extend and, most importantly, reduces costs to ~20%. We have used the enzyme marketed by New England Biolabs and can be purified from a strain from hot springs in Rotorua, New Zealand. Protocol is as above, except 93° C. for 5 min, add 50 µl liquid paraffin to prevent evaporation, then: add 4 U polymerase and incubate in 50° C. bath for 30 s, 63° C. bath for 90 s, and 93° C. bath for 30 s. Repeat this cycle e.g. 50 times.

Detection of viral DNA produced by PCR procedure

A number of approaches are possible from this point on. Some of those we use are described.

A. POLYACRYLAMIDE GEL ELECTROPHORESIS FOR DIRECT VISUALIZATION OF PCR PRODUCTS

1. Pour a 12% non-denaturing polyacrylamide gel.

2. When the gel has set load half of each PCR mixture (50 µl) and electrophorese for 2 h at 15 V/cm. Include 0.5 µg of a pBR322/HpaII digest as molecular weight marker.

3. After electrophoresis immerse gel in ethidium bromide solution (50 µg/ml in distilled water) and allow to stain for 30 min.

4. Sample(s) positive for HPV16 or HPV33 show as a discrete band of approximately 200 bp. Samples positive for HPV6 or HPV11 show as a discrete band of approximately 120 bp. Samples positive for HPV6/11 and HPV/16/33 show as discrete 200 bp and 120 bp bands.

OR

B. ALKALINE PHOSPHATASE OLIGONUCLEOTIDE PROBE ONTO DOT BLOT

1. Application of samples to membrane i) Place 25 µl of sample in an Eppendorf tube. Add 25 µl of 1.0 M sodium hydroxide solution, followed by 12.5 µl of distilled water.
   ii) Place tube in 95–98° C. water bath for 3 minutes.
   iii) Apply all of mixture to nylon membrane provided using Hybri-dot ® manifold.
   iv) Rinse with 2 x SSC.
   v) Allow membrane to dry.

2. Probing membrane with alkaline phosphatase-linked oligonucleotide probe i) Prehybridization - Place membrane in plastic; bag provided and add 10 ml of prehybridization solution. Seal bag and incubate at 30° C. for 40 min with agitation.
   ii) Hybridization - Empty contents of bag and replace with 10 ml of hybridization solution. Reseal plastic bag and incubate at 30 C. for 40 min with agitation.
   iii) Washing - Remove membrane from bag and place in a dish containing 500 ml of wash solution 1 preheated to 37° C.. Agitate for 10 minutes at this temperature. Replace solution with 500 ml of wash solution 2 and agitate for a further 10 min at 37° C.. Replace solution yet again, this time with 200 ml of wash solution 3, and agitate for 5 min at room temperature. Repeat the wash solution 3 step five more times
   iv) Colour development - Place membrane in shallow dish containing 25 ml of colour reagent solution. Allow colour to develop for several hours or overnight at room temperature.

OR

C. RADIOACTIVE OLIGONUCLEOTIDE PROBE ONTO DOT BLOT i) Prehybridization The membrane is prehybridized for at least 1 h at 30° C.

Several approaches can be used for this.

(a) One uses a specially designed perspex block constructed in the Laboratory's mechanical workshop. The block is stood upright in a 30° C. water bath with the membrane, bathed in the following solution, inside.

(b) Another approach is to cut out two sheets of Whatman type 542 paper to dimensions slightly larger than the membrane. Next, place membrane on top of one sheet and wet membrane with 2 ml prehybridization solution. Then place other sheet of Whatman on top and place the resulting 'sandwich' in a plastic bag with the rest of the prehybridization solution.

| Prehybridization mixture: (10 ml total volume) | |
|---|---|
| 10% (wt./vol) non fat milk powder (e.g., Diploma ®) | 0.5 ml |
| 20x SSC (3M NaCl, 0.3 M sodium citrate) | 2.5 ml |
| 20% (wt./vol) SDS (sodium dodecyl sulphate) | 0.5 ml |
| 10 mg/ml carrier DNA (e.g., from herring sperm) | 2.0 ml |
| Sterile distilled water | 4.5 ml | ii) Hybridization Pour off prehybridization mixture and replace with hybridization mixture, which is the same except for the addition of radioactively labelled viral DNA (1 ng/ml hybridization mixture).

Hybridization is allowed to proceed overnight at 30° C. in the perspex block or plastic bag.

iii) Washing membranes Membrane filters are washed under conditions of high stringency. This is to remove all radioactive DNA probe except that which is attached specifically, by hydrogen bonding, to identical viral DNA sequences that may be present within a sample.

iv) Autoradiography

1. The membrane is blotted with filter paper, but not allowed to dry, and while still moist, is taped to a sheet of 3MM Whatman paper, then covered with cling wrap.

2. This is applied to a suitable x-ray film (e.g., Kodak XR-5) in a dark-room and sealed in an autoradiography cassette with two intensifying screens (DuPont).

3. Autoradiography is allowed to proceed at −80° C. for 2.5–12 h.

4. Dark spots on the autoradiograph indicate the presence of HPV type.

PROTOCOL FOR WARTS AND BIOPSIES

Reagent preparation

Prepare lysis buffer by adding 1 ml distilled water to lysis buffer powder and then mixing it with the enzyme powder in vial.

Sample preparation

1. Rinse tissue 3 times in 500 µl collection buffer (as above for scrapes).

2. Cut tissue into ~1 mm pieces.

3. Add to tissue 700 µl lysis buffer enzyme solution.

4. Leave at 37° C. until tissue appears completely digested or overnight at 37° C.

5. Add 350 µl deproteinization reagent 1 and 350 µl deproteinization reagent 2. Mix vigorously.

6. Microfuge for 15 seconds and remove top layer into a fresh tube (discard lower phase).

7. Repeat steps 5 and 6 three times.

8. Add 700 µl of deproteinization reagent 2, mix and microfuge for 15 seconds.

9. Remove top layer into a fresh tube and add 100 µl of extraction solution. Immediately add 1,4 ml of ice-cold absolute ethanol. Place at −20° C. for 1 hour or −80° C. for 15 minutes.

10. Microfuge for 10 minutes and then pour off ethanol carefully. Allow pellet (=DNA) to dry for 15 minutes.

11. Resuspend DNA in 50 ml of TE and, if possible, determine DNA concentration at 260 nm using a spectrophotometer. (1 O.D.$_{260}$ unit=50 µg/ml).

Procedure for polymerase chain reaction (PCR)

1. Add a volume of DNA solution that contains ~1 µg of DNA to 100 µl of PCR reaction mixture in an Eppendorf tube.

2. Place tube in water bath heated to 95–98° C.

3. After 10 min microfuge tube briefly (~5 seconds) to remove condensation.

4. Place tube in water bath preheated to 37° C.

5. After 2 min add 1 µl of DNA polymerase solution and continue 37° C. incubation for 2 min.

6. Place tube back in 95–98° C. water bath for 2 min.

7. Repeat steps 4–6 twenty five times.

Detection of viral DNA produced by PCR procedure

See as above for scrapes protocols.

Standards and controls

Standards: Pure viral DNA of HPV6, HPV11, HPV16, HPV18 and HPV33 or oligonucleotides corresponding to at least the hybridizing target region of each HPV are added to the membrane in amounts of 125, 12.5, 1.25 and 0.125 pg for complete HPV or correspondingly less for oligonucleotides.

Controls:

i) Neonatal foreskin DNA (detects the unlikely occurrence of any nonspecific hybridization to human skin DNA) in amounts of 10 ng, 50 ng, 100 ng and 2 µg is applied to each membrane.

ii) Positive control: DNA from HPV6/11 and HPV16/18/33 infected samples.

iii) Alu-repeated sequence DNA (to hybridize to the Alu probe) in amounts of 10 pg, 50 pg, 100 pg and 2 ng is applied to each membrane. (Optional)

Automation

We have designed and constructed a working prototype machine for performing the PCR reaction automatically.

Total Time for Test Result (After receipt of samples in lab.)

Several hours-2 days.

Results Obtained with the Test

Results have indicated the importance of direct HPV detection in patient evaluation. For example, many patients that had normal cytology of cervical cells were found to be infected with the carcinogenic varieties of HPV. This may reflect the fact that our test can detect infection at an earlier stage, perhaps even before the virus has had a change to cause a morphological change in the cell. Moreover, the lesions associated with the potentially carcinogenic varieties of HPV are often flat, rather than the large obvious condylamas caused by the more benign varieties, and are therefore not as easily seen in the clinic.

SPECIFIC EXPERIMENTS REPRESENTING EXAMPLES OF METHOD IN OPERATION

Drawings are given in the figures in lieu of photographs as the photocopying process gives poor resolution.

A. PCR amplification of pure HPV16 viral DNA using normal Klenow. 1 ng HPV16/pBR322 was subjected to 20 rounds of: 95° C. for 2 min (strand dissociation), then 37° C. for 2 min (annealing), then 1 U Klenow enzyme added and 37° C. incubation for 2 min. Half (50 µl) of the resulting mixture was electrophoresed on a 2% agarose gel and the result is shown in FIG. 1. Amount=2.5×100 ng=250 ng. Region amplified=¼₀th of total HPV16 sequence. Total amplification=250×40=10,000 x, (i.e., efficiency of reaction was 60% for each cycle).

Figure 2:
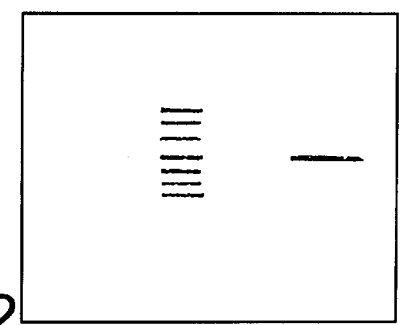
FIG. 2 indicates the amplification of HPV16 DNA from wart biopsy relative to a standard restriction of pBR322 with HpAII.
Figure 3:
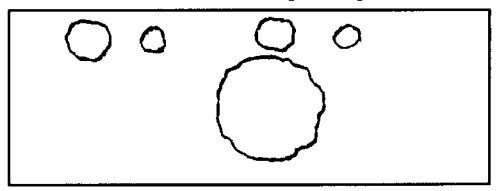
FIG. 3 indicates the hybridization of 32P-labeled HPV16/13 target oligonucleotide probe with PCR amplified HPV 16 DNA from wart biopsy.

B. PCR amplification of wart biopsy DNA with HPV16/33 test. The DNA of anal wart Gap289 was phenol/chloroform extracted and ethanol precipitated. 1 µg of DNA was then subjected to 23 rounds of amplification (each: 95° C. for 2 min, then 37° C. for 2 min, 1 U Klenow added and 37° C. for 2 min). 40% (50 µl) was electrophoresed on a 2% agarose gel. Ethidium bromide stained DNA is shown in FIG. 2. The PCR sample and standards were spotted onto a membrane and hybridization performed overnight with $^{32}$P-labelled HPV16/33 target oligonucleotide probe. Wash conditions were 22° C. for 5 min, then 38° C. for 10 min in 5 x SSPE/0.1% SDS. Result of autoradiography is shown in FIG. 3. Note that amounts are for recombinant viral DNAs used, only a fraction of which represents amplified sequence, within which is the target hybridization region.

Figure 4:
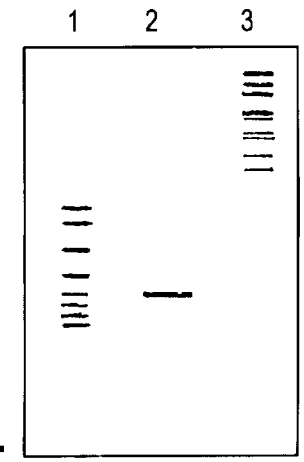
FIG. 4 indicates the amplification of pure HPV 16 recombinant viral DNA using PCR (Lane 1) relative to standard DNA size markers (Lane 2 - pBR322 cut with HpAII; Lane 3 - pBR322 cut with SPP-1).
Figure 5:
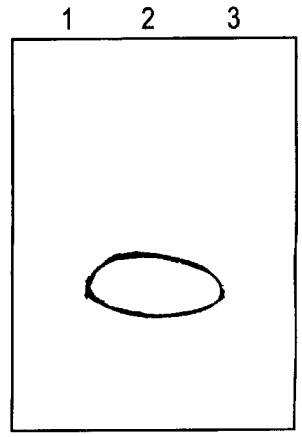
FIG. 5 indicates the hybridization of HPV16/33 oligonucleotide probe with HPV16 DNA taken from Lane-2 of FIG. 4.

C. PCR amplification of pure HPV16 recombinant viral DNA using normal Klenow, 1 ng of HPV16/pBR322, 10 mM Tris.HCl, pH 7.6, 10 mM MgCl$_2$, 50 mM NaCl 500 ng of each of the HPV16/33 primers, 4 µl of each dNTP (50 mM stock). 23 rounds of: 98° C. for 2 min, then 37° C. for 2 min, add Klenow, then 37° C. for 2 min. Electrophoresis on 2% agarose gel. Ethidium bromide stained gel is shown in FIG. 4. Lanes 1 and 3 are DNA size markers, viz. pBR322 cut with HpaII and SPP-1, respectively. A single DNA band of the expected size (~200 base pairs) can be seen in lane 2. To prove this Southern blotting was then performed on this gel, using for hybridization conditions: 5 x SSPE, 2% SDS, 0.5 ml BLOTTO, 0.5 ml of 10 mg/ml salmon sperm DNA, 5.5 ml distilled water. Prehybridization was for 1 h at 30° C. and hybridization was overnight at 30° C. in the above solution with ~1 ng/ml of end-labelled target HPV16/33 oligonucleotide probe. Washing was for 10 min at 38° C. in 1 x SSPE, 0.1% SDS. Result in FIG. 5, showing massive hybridization to a band at the expected position in lane 2 (i.e., at the same position as the band of stained DNA in FIG. 4 lane 2).

Figure 6:
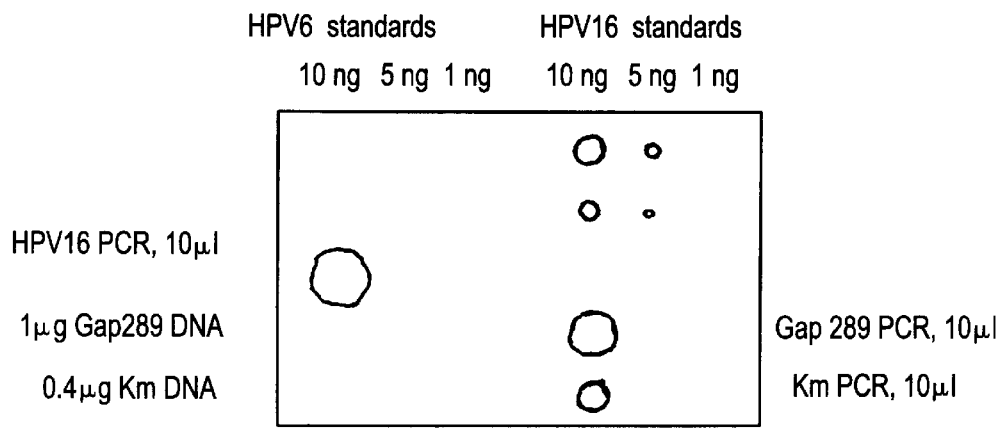
FIG. 6 indicates the hybridization of HPV16/33 oligonucleotide probe with PCR amplified HPV16 DNA from anal wart biopsies.

D. Biopsies of anal warts. Patient specimens: Gap119, Gap278, Km, Gap289, 11912C. Conditions as described above in C. FIG. 6 is an autoradiograph after radioactive probing: Km and Gap289 were +ve, i.e., contained HPV16.

E. Southern blot of biopsies +ve for HPV16. This experiment shows that the HPV16/33 oligo probe hybridizes to the correct restriction fragments in unamplified biopsies and pure viral DNA; also that there is no cross hybridization to other HPV types.

Lane 1—8 µg Gap289 cut with BamHI/PstI
Lane 2—blank
Lane 3—100 ng HPV33 cut with BglII/PstI
Lane 4—100 ng HPV16 cut with BamHI/PstI
Lane 5—100 ng HPV18 cut with EcoRI/XbaI
Lane 6—100 ng HPV11 cut with BamHI/PstI
Lane 7—100 ng HPV6 cut with EcoRI/PstI The autoradiograph (shown diagrammatically in FIG. 7) shows hybridization of radioactive HPV16/33 oligo probe to HPV16 in lane 4 and to HPV33 in lane 3. No hybridization occurred to HPVs 6, 11 and 18 in lanes 7, 6 and 5, respectively, showing that the probe is specific for HPVs 16 and 33. Hybridization in lane 1 shows that specimen Gap289 contained HPV16.

Figure 8:
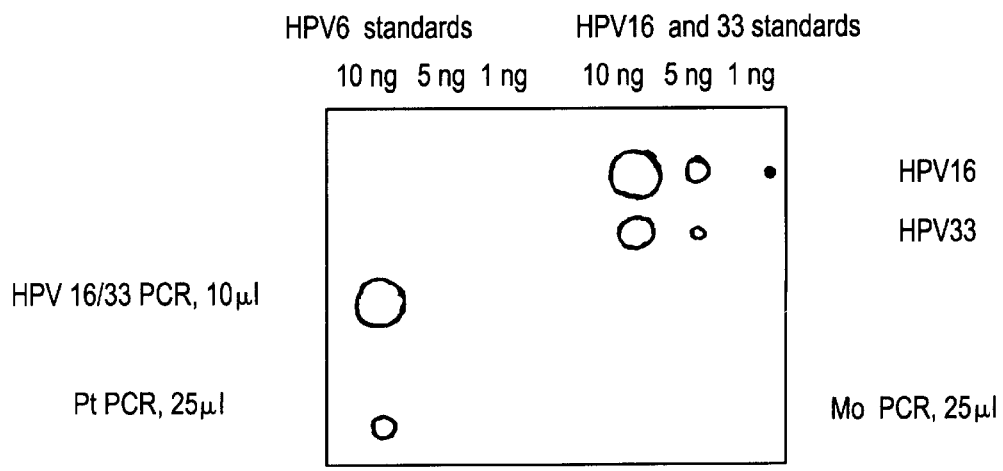
FIG. 8 indicates the hybridization of radioactively labeled HPV16/33 oligonucleotide probe with PCR amplified DNA from cervical scrapes.

F. Cervical scrapes—HPV16/33 PCR amplification. This shows the technique can detect specific HPV in scrape specimens. Scrapes: Pt and Mo. ~10,000 cells were suspended in 35 µl water, heated to 98° C. for 10 min, 65 µl PCR mixture added and normal protocol followed with 30 rounds of amplification using normal Klenow. Samples were dotted onto membranes and probed with radioactive oligo probe. Result (FIG. 8): Pt scrape was +ve with HPV16/33 probe, Mo was −ve.

Figure 7:
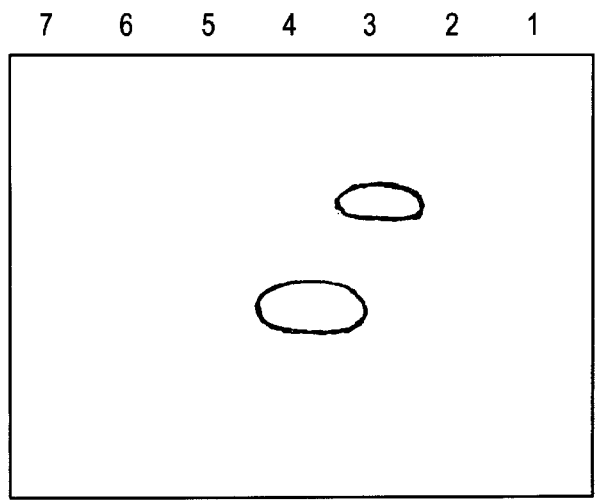
FIG. 7 indicates that the HPV 16/33 oligonucleotide probe hybridizes to the correct restriction fragments of unamplified biopsies (Lanes 1,3,4,).

G. Souther blot of scrape. This was to confirm that Pt scrape had given real amplification, (i.e., is proof of validity of result in H.) Gel used was 1.5% agarose. In FIG. 7:
Lane 1—25 μl Pt PCR digested with Bg/I/BamHI in PCR buffer.
Lane 2—40 ng of HPV33 insert.
Lane 3—40 ng of HPV16 insert.
Lane 4—0.5 μg of pBR322 digested with HpaII.
Lane 5—Bacteriophage λdigested with HindIII.

Figure 9:
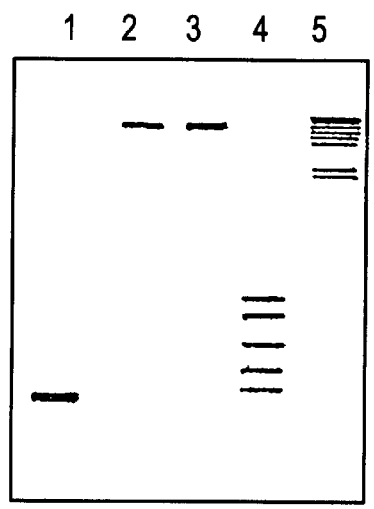
FIG. 9 indicates the amplification of the cervical scrape DNA used in FIG. 8 (Pt. cervical scrape) using PCR.
Figure 10:
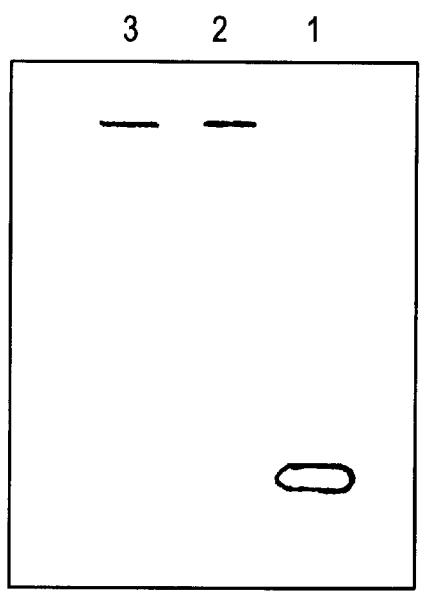
FIG. 10 indicates the hybridization of radioactively labeled HPV16/33 oligonucleotide probe with PCR amplified Pt. Cervical scrape.
Figure 11:
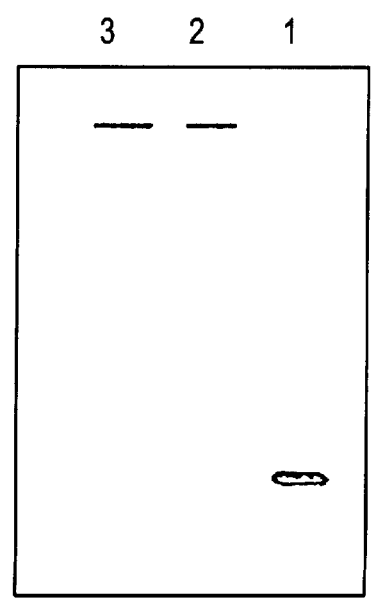
FIG. 11 indicates the hybridization of alkaline phosphatase labeled HPV16/33 probe with the PCR amplified Pt. Cervical scrape.

FIG. 9 depicts the stained gel result. FIG. 10 shows the result of radioactive target oligo probing. FIG. 11 shows the result of alkaline phosphatase target oligo probing. A dark band of hybridization can be seen at the correct position in lane 1 for the patient specimen's PCR products and bands in lanes 2 and 3 corresponding to the position of the whole virus. This confirms the presence of HPV16 in the cervical scrape.

The following examples (H–J) show additional positive results with the technique used on various biopsies and scrapes.

Figure 12:
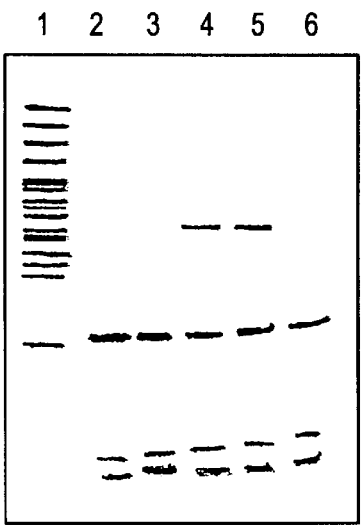
FIG. 12 indicates the PCR amplification of HPV6/11 DNA from various biopsies and scrapes.
Figure 13:
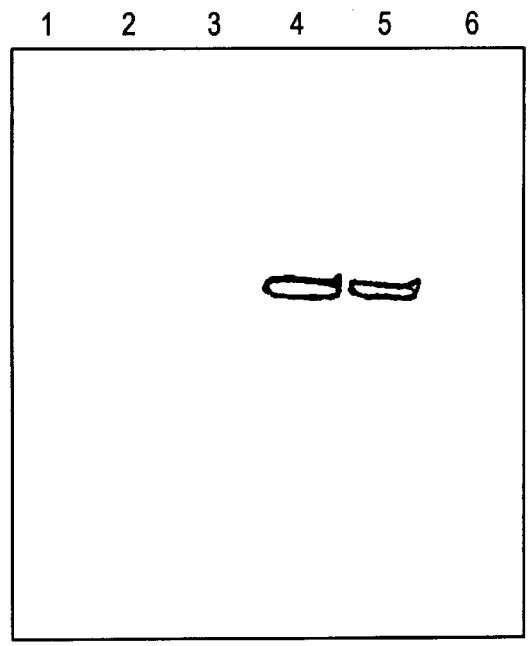
FIG. 13 indicates the hybridization of radioactively labeled HPV6/11 oligonucleotide probe with PCR amplified DN from cervical scrape (Lane-4) and vaginal scrape (Lane-5).

H. Various scrapes and anogenital wart biopsies—HPV6/11 PCR. In FIGS. 12 and 13:
Lane 1—0.4 μg pBR322 cut with HpaII.
Lane 2—0.9 μg F9885 wart DNA, HPV/6/11 oligos only.
Lane 3—1 μg Ow wart DNA, HPV6/11 and HPV16/33 oligos.
Lane 4—3 μl cells from F11912 cervical scrape, HPV6/11 oligos only.
Lane 5—3 μl cells from F11912 vaginal scrape, HPV6/11 oligos only.
Lane 6—5 μl cells from F11912 rectal scrape, HPV6/11 oligos only.

30 rounds were performed under normal protocol conditions, 50 μl of each PCR mixture was loaded on a 12% non-denaturing polyacrylamide gel. The stained gel is shown in FIG. 12. (The band at ~34 bp is an artifact associated with the HPV6/11 primers.) This membrane was electroblotted at 20V/100 mA for 1 h and probed with the radioactive HPV6/11 oligo probe. Result of 2 h exposure to x-ray film is shown in FIG. 13. Bands in lanes 4 and 5 indicate that cervical and vaginal, but not rectal cells from this patient were infected with HPV6/11.

Figure 14:
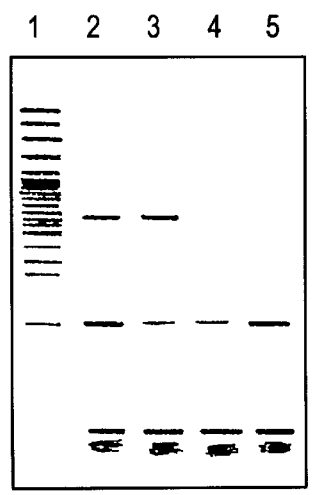
FIG. 14 indicates the PCR amplification of HPV6/11 DNA from various wart biopsies.

I. Warts—HPV6/11 PCR. Results are shown in FIG. 14:
Lane 1—pBR322 cut with HpaII
Lane 2—750 ng of F8408 labial wart
Lane 3—1 μg Gap252 anal wart
Lane 4—860 ng Tr anal wart
Lane 5—750 ng Bi anal wart
(Conditions: 25 rounds, HPV6/11 primers only; 50 μl of each PCR mix run on gel.)

Figure 15:
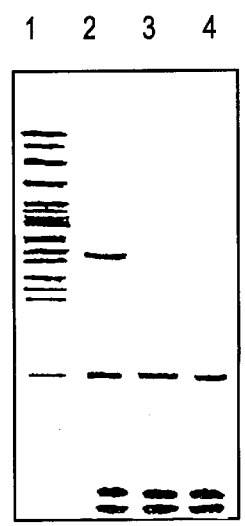
FIG. 15 indicates the PCR amplification of HPV6/11 DNA from Hn biopsy.

J. Cervical warts—HPV6/11 and HPV16/33 primers. 50 μl run on 12% polyacrylamide gel, results as shown in FIG. 15.
Lane 1—pBR322 cut with HpaII
Lane 2—~500 ng Hn biopsy
Lane 3—~500 ng Hs biopsy
Lane 4—~500 ng Ls biopsy K. Cervical scrapes—HPV6/11 and HPV16/33. This example shows that primers for different HPVs can be used together in the same reaction mixture to generate amplification products unique for each HPV type. Results are shown in FIG. 16.

Lane 1—pB322 cut with HpaII.
Lane 2—1 ng of HPV6/pAT153 and 1 ng of HPV16/pBR322; HPV6/11 and HPV16/33 primers.
Lane 3—3 μl cells of CSC019 scrape. HPV6/11 and HPV16/33 primers.
Lane 4—3 μl cells of CSC328 scrape. HPV6/11 primers.
Lane 5—3 μl cells of Pt scrape, HPV6/11 primers.

(Conditions: 25 rounds, normal protocol conditions.) In lane 2 of FIG. 16 one can see the 200 bp HPV16/33 amplification product (faint) and the 120 bp HPV6/11 product (darker). Lanes 3–5 were negative (only primer bands seen), i.e., did not contain HPV6/11.

Figure 20:
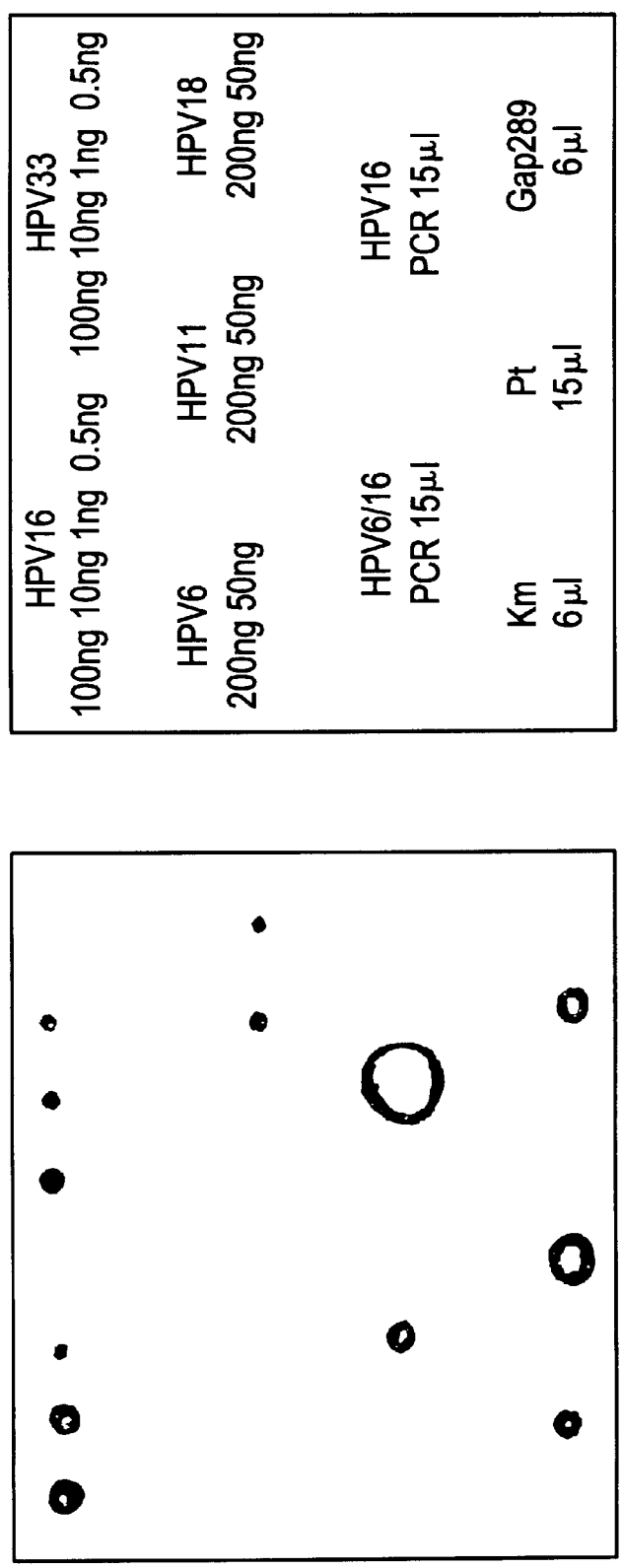
FIG. 20 is a dot blot indicating the hybridisation of radioactively labelled probes with various HPV types.

L. Scrapes and biopsies—HPV16/33 PCR. This experiment is a comparison of radioactive and nonradioactive probing for the detection of HPVs by the PCR method. In FIG. 12:
Lane 1—pBR322 cut with HpaII
Lane 2—Blank
Lane 3—HPV6/pAT153 and HPV16/pBR322 PCR from 1
Lane 4—15 μl of Km PCR
Lane 5—15 μl of Gap289 PCR
Lane 6—15 μl Pt scrape PCR Gel (12% polyacrylamide) was run and stained (FIG. 17), then electroblotted and probed with alkaline phosphatase (FIG. 18), and radioactive (FIG. 19) HPV16/33 oligo probe. In FIG. 17 the ~200 bp band indicative of HPV16/33 can be seen in lanes 6, 5, 4, and 3 and the 120 bp HPV6/11 band can be seen in lane 3. In FIG. 18 a single band of hybridization to the ~200 bp HPV16/33 amplification products can be seen in each of lanes 6–3. FIG. 19 shows the result of a 1.5 h exposure to the x-ray film: hybridization can be seen to the ~200 bp HPV16/33 amplification products. FIG. 20 is a dot blot probed with radioactive target oligo probe (Right: diagram of position of samples on dot blot; Left: result of hybridization).

Figure 21:
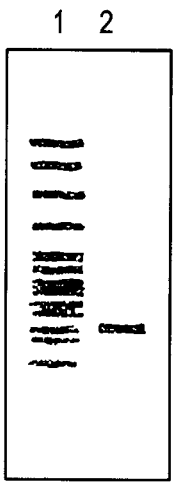
FIG. 21 indicates that heat stable polymerase from *Thermus Aquaticus* is able to be used to amplify HPV DNA.
Figure 22:
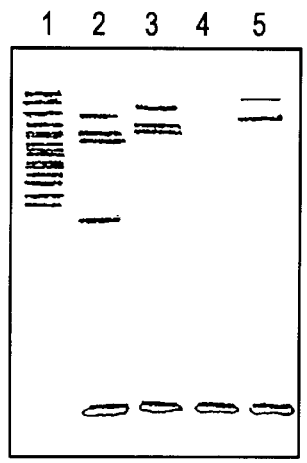
FIG. 22 indicates that heat stable polymerase from *Thermus Aquaticus* is able to amplify HPV16 DNA from biopsies.

M. Heat stable polymerase—HPV6 PCR. 1 ng HPV6/pAT153, 2 units of *Thermus aquaticus* DNA polymerase added initially and after every 10 rounds for 40 rounds. The conditions used were exactly as specified in the New England Biolabs protocol. The result (FIG. 21) demonstrates that the heat stable polymerase is also able to produce the desired amplification products. In this figure:
Lane 1—pBR322HpaII
Lane 2—40 μl of HPV6/pAT153 PCR N. Heat stable polymerase—HPV16 and biopsy. After amplification HPV16/pBR322 cut with HinfI should give 2 fragments of 52 bp and 142 bp. 5 ng HPV33/plink and 1 μg Gap289 were subjected to 40 rounds with heat stable polymerase (lanes 4 and 5 in FIG. 22). The conditions used were: 50 mM Tris.HCl, pH 8.8 at 25° C., 10 mM MgCl$_2$, 10 mM (NH$_4$)$_2$SO$_4$, 10 μl DSMO, 500 ng of each HPV16/33 primer, 4 μl of each dNTP (50 mM stock), and 50 μl liquid paraffin, 4 U DNA polymerase was added at the start. Incubation was in 93° C. incubator for 30 s, then 50° C. for 30 s, then 63° C. for 45 s. In FIG. 22:
Lane 1—pBR33/HpaII
Lane 2—HPV16/pBR322 cut with HinfI (20 μl) PCR+2 μl 10 x HinfI buffer+1 μl enzyme+6 μl dH$_2$O)
Lane 3—20 μl of HPV16/pBR322 PCR
Lane 4—20 μl of HPV33/plink PCR
Lane 5—20 μl of Gap289

Figure 23:
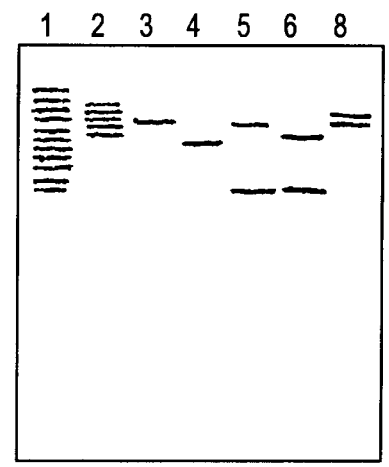
FIG. 23 indicates that HPV DNA from diluted biopsies was amplified using PCR.
Figure 24:
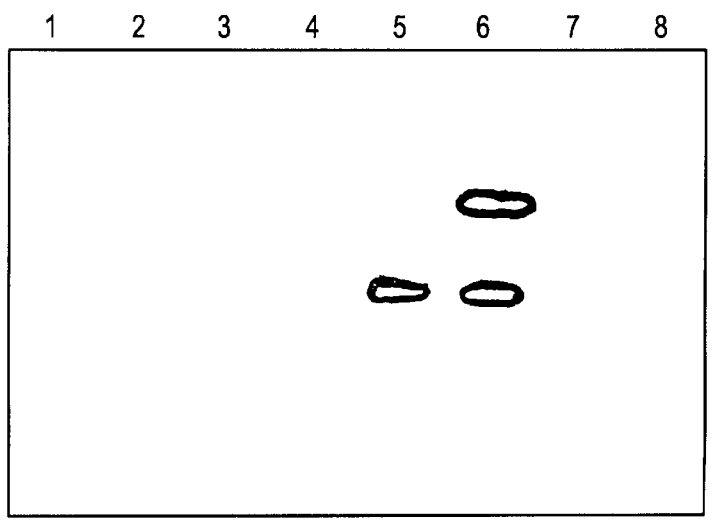
FIG. 24 indicates the amplified DNA from the diluted hybridising with radioactively labelled HPV6/11 oligonucleotide probe.
Figure 25:
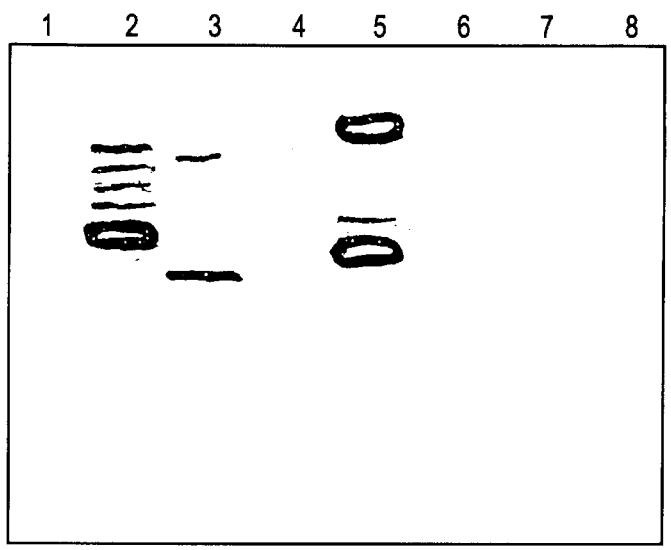
FIG. 25 indicates the amplified DNA from the diluted biopsies hybridising with radioactively labelled HPV16/33 oligonucleotide probe.

O. Diluted biopsy. 100 PCR rounds using heat stable polymerase. Wart biopsy Gap289 (1 μg/μl) was diluted 1:10$^3$, 1:10$^6$ and 1:10$^9$ and 100 rounds of amplification were performed using 1 μl of each dilution and 4 U of heat stable DNA polymerase initially, then an additional 2 U added after 50 rounds. Other biopsies and scrapes were subjected to 50 rounds only. Conditions were as in example P. The result shows the extreme sensitivity of the test: the best results with this excessive number of rounds of amplification were obtained with the most dilute sample. FIG. 23 shows the ethidium bromide stained DNA gel. The gel was electroblotted and probed with radioactively labelled HPV6/11 (FIG. 24) and HPV16/33 (FIG. 25) target oligo probe. The result shows the extreme specificity of the test. In FIG. 15(b) it can be seen that only in lane 5 and 6 where HPV6/11 primers were used was there hybridization to a 120 bp band, the size of the HPV6/11 amplification product. Absolutely no hybridization was seen in the lanes where samples had been amplified using only HPV16/33 primers. In FIG. 15(c) hybridization to the ~200 bp band of HPV16/33 amplification products can be seen for the biopsy (lanes 2–4) and the anal scrape (lane 5). In FIGS. 23, 24 and 25 the lanes are as follows:

Lane 1—pBR322 cut with HpaII
Lane 2—Gap289 (1:10$^3$) PCR (HPV16/33 primers only)
Lane 3—Gap289 (1:10$^6$) PCR (HPV16/33 primers only)
Lane 4—Gap289 (1:10$^9$) PCR (HPV16/33 primers only)
Lane 5—Anal scrape Gap402 PCR (HPV6/11 and HPV16/33 primers)
Lane 6—Bs wart PCR (HPV6/11 and HPV16/33 primers)
Lane 7—Cervical scrape 11912 (HPV16/33 primers only)
Lane 8—Vaginal scrape 11912 (HPV16/33 primers only)

Figure 26:
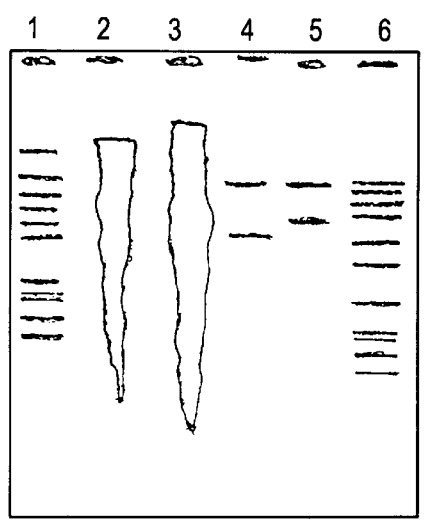
FIG. 26 indicates unamplified HPV16, HPV33 and biopsies, run on a gel and stained with ethidium bromide.
Figure 27:
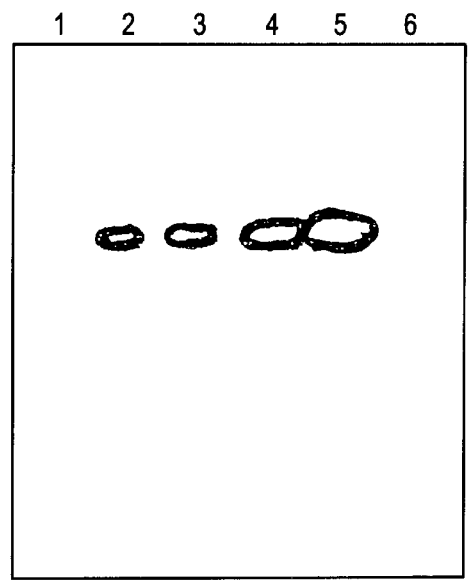
FIG. 27 indicates the hybridisation of HPV16/33 oligonucleotide probe with unamplified HPV16, HPV18 and biopsies.
Figure 28:
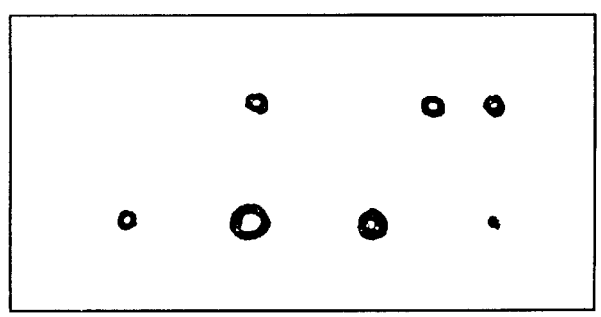
FIG. 28 indicates hybridisation of alkaline phosphatase labelled HPV16/33 oligonucleotide probe with HPV16 DNA.

P. Hybridization of target oligo probe to unamplified HPV16, HPV33 and biopsies. Ordinary restricted HPVs and biopsies were run on a gel and stained (FIG. 26), then probed with HPV16/33 target oligo probe. Result is shown in FIG. 27, where hybridization can be seen in each case (lanes 2–5) and to correct restriction fragment in the case of recombinant viral DNA. Six days of exposure to x-ray film were required for this unamplified DNA. In FIGS. 26 and 27:

Lane 1—Bacteriophage λcut with HindIII/EcoRI
Lane 2—5 μg Bs wart DNA, Bg/II/BamHI
Lane 3—5 μg Gap289, Bg/II/BamHI
Lane 4—HPV16/pBR322, BamHI
Lane 5—HPV33/plink, Bg/II
Lane 6—SPP-I Q. Dot blots showing hybridization of HPV16/33 alkaline phosphatase oligo probe to HPV16 are shown in FIG. 28.

Figure 29:
FIG. 29 indicates the amplification of HPV18 DNA using PCR.

R. HPV18 PCR. 30 rounds with normal Klenow DNA polymerase Result is shown in FIG. 29, where the lanes are:
Lane 1—HPV16 insert PCR products; HPV16/33 primers.
Lane 2—HPV18 insert PCR products; HPV18 primers used.

The HPV18 PCR products of ~100 bp can be seen in lane 2. In lane 1 are the HPV16 PCR products of ~200 bp.

What is claimed is:

1. A method for distinguishing between high risk strains 16 and 33 or 18 of human papillomavirus and low risk strains 6 and 11 of human papillomavirus in a sample of human cervical tissue comprising:
    a) obtaining DNA from the human cervical tissue sample,
    b) simultaneously or individually adding oligonucleotide primer pairs which are specific for the E6 region of i) HPV 16 and 33, ii) HPV 18 or iii) HPV 6 and 11,
    c) amplifying the HPV E6 region by polymerase chain reaction using the E6 specific primer pair(s) and
    d) detecting the presence or absence of amplification products specific for HPV16 and 33 or 18 or HPV 6 and 11 to thereby distinguish between the presence of high risk strains HPV 16 and 33 or 18 and low risk strains HPV 6 and 11.

2. A method according to claim 1 wherein the amplification products are detected using a labeled oligonucleotide hybridization probe.

3. A method according to claim 2 wherein the oligonucleotide probe is labeled with a $^{32}$P radioactive label.

4. A method according to claim 2 wherein the oligonucleotide probe is labeled with an alkaline phosphatase enzyme label.

* * * * *